United States Patent

Cheng et al.

[11] Patent Number: 5,844,062
[45] Date of Patent: Dec. 1, 1998

[54] PROCESS FOR PREPARING PHENOLEPOXY RESINS IN THE ABSENCE OF AN AQUEOUS PHASE

[75] Inventors: Kung-Lung Cheng; Woan-Shiow Tzeng, both of Hsinchu; Shu-Chen Lin, Yi-Lang, all of Taiwan

[73] Assignee: Industrial Technology Research Institute, Hsinchu, Taiwan

[21] Appl. No.: 841,728

[22] Filed: Apr. 29, 1997

[51] Int. Cl.[6] ............................. C08G 59/06; C08G 59/08
[52] U.S. Cl. ............................................. 528/94; 549/517
[58] Field of Search ................................ 549/517; 528/94

[56] References Cited

U.S. PATENT DOCUMENTS

| | | | |
|---|---|---|---|
| 2,943,096 | 6/1960 | Reinking | 549/517 |
| 4,582,892 | 4/1986 | Chang et al. | 528/93 |
| 5,278,260 | 1/1994 | Schaffner et al. | 525/507 |

*Primary Examiner*—Frederick Krass
*Attorney, Agent, or Firm*—W. Wayne Liauh

[57] ABSTRACT

A process for preparing phenolepoxy resin represented by the following formula:

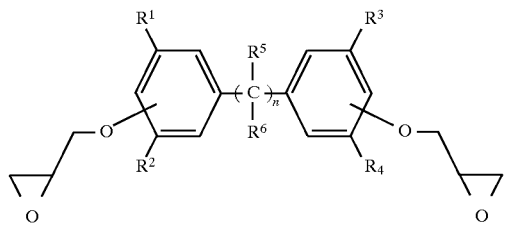

wherein: (a) $R^1$, $R^2$, $R^3$, and $R^4$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; (b) $R^5$ and $R^6$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups;

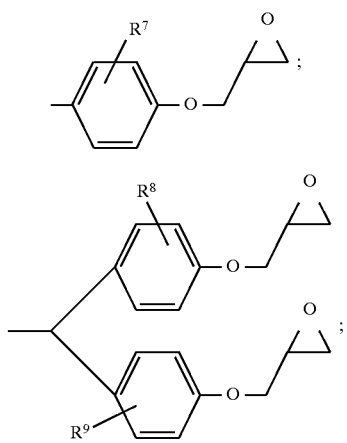

(c) $R^7$ is hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; (d) $R^8$ and $R^9$, which can be the same of different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; and (e) n is an integer of 0 or 1. The phenolepoxy resin can be advantageously used in making packaging materials for ICs, as a substrate additive for printed circuit boards, and as adhesive for the electronic industry. The process includes the steps of preparing a reaction medium which contains only polyphenol, epihalohydrinl and an imidazole catalyst, and then causing the reaction medium to react in the absence of an aqueous phase.

6 Claims, No Drawings

5,844,062

PROCESS FOR PREPARING PHENOLEPOXY RESINS IN THE ABSENCE OF AN AQUEOUS PHASE

FIELD OF THE INVENTION

The present invention relates to a new family of epoxy resins. More specifically, the present invention relates to a family of novel phenolepoxy resins which are prepared from a greatly simplified, and thus more cost-effective, process but which exhibit the kind of mechanical and adhesive properties that are at least as good as those of other high-performance commercially available epoxy resins such as epoxy cresol-novolac resins, etc. The phenolepoxy resins disclosed in the present invention are most advantageous for use in IC packaging, including encapsulation, in making printed circuit boards, and as adhesives in making electronic components, etc. The present invention also relates to the novel process for making the phenolepoxy resins.

BACKGROUND OF THE INVENTION

Epoxy resins are characterized by the presence of a three-membered cyclic ether group commonly referred to as an epoxy group, 1,2-epoxide, or oxirane. The most widely used epoxy resins are diglycidyl ethers of bisphenol A, derived from bisphenol A and epichlorohydrin. They are most frequently cured with anhydrides, aliphatic amines, or polyamides, depending on desired properties. Epoxy resins have been known to convey outstanding performance characteristics. However, various multifunctional resins, including epoxy cresol novolac resins (ECN) and polynuclear phenol-glycidyl ether-derived resins have been developed to further improve high temperature performance and other select properties.

Epoxy resins have played a very important role in the advancement of the information industry. A variety of epoxy resins, especially the o-cresol epoxy novolac resins, for example, have been widely used for the encapsulation of semiconductor devices and as adhesives in the microelectronic industry. Typically, liquid epoxy resins are synthesized by a two-step process in which an excess of epichlorohydrin is reacted with bisphenol A in the presence of at least a stoichiometric quantity of an alkaline catalyst, such as aqueous solutions of sodium hydroxide. The first step of the epoxy resin synthesis involves the formation of an intermediate, which is the dichlorodydrin of bisphenol A, and the second step involves a further reaction via dehydrohalogenation of the intermdeiate, again, with a stoichiometric quantity of alkali.

A number of improvements have been proposed in the prior art to improve the epoxy resin synthesis process. In U.S. Pat. No. 5,028,686, it was disclosed a concurrent addition process for preparing high purity epoxy resins in which epoxy resins which are relatively low in total bound halide are prepared by concurrently and continuously adding a mixture of (1) a mixture of an epihalohydrin, a compound containing an average of more than one group reactive with a vicinal epoxide group and a solvent and (2) an aqueous or organic solution of an alkali or alkaline earth metal hydroxide; to a mixture of epihalohydrin and a solvent.

U.S. Pat. No. 4,954,603 disclosed a process for making fire-retardant epoxy resins by reacting a trifunctional epoxy compound with halogenated bisphenol A in the presence of a catalyst, which comprised sodium hydroxide in a molar ratio of 2.85 to 1 relative to the trifunctional epoxy compound.

European Patent 579301 disclosed a process for producing 4,4'-biphenyl skeleton-containing epoxy resins, by reacting 4,4'-biphenol with a epihalohydrin in a reaction medium of glycol monoethers. During the reaction, an alkali metal hydroxide was gradually added to the reaction mixture. The total amount of alkali metal hydroxide added was between 0.8 and 2.0 moles per mole of phenol groups.

European Patent 396203 disclosed an epoxy resin encapsulation composition comprising a tetrakisglycidyl ether of an $\alpha,\alpha,\omega,\omega$-tetrakis(hydroxyphenyl)$C_4$–$C_{24}$ alkane. The tetrakisglycidyl ether was produced by reacting an appropriate tetraphenol with a halohydrin in the presence of an alkali metal hydroxide.

All the above mentioned patents involved, or at least claimed, certain improvement over the conventional methods. However, all of them still share a common characteristic of the conventional methods in that all the claimed processes still involved the addition of a strong base, which typically contained an alkali metal hydroxide in an aqueous solution, or in a mixture of water and an alcohol solvent (such as isopropanol or butanediol, into the reaction mixture, which typically contained a polyphenol (bi-, tri-, or tetraphenol) and epihalohydrin. The amount of alkali metal hydroxide required is at least a stoichiometric quantity of the phenol groups (i.e., every mole of phenol group would require at least one mole of alkali metal hydroxide in a one-to-one quantitative substitution reaction).

One of the disadvantages of the conventional processes in preparing epoxy resins is that, because the addition of the strong base of alkali metal hydroxide is exothermic, it must be gradually added, as reported in all the references mentioned above. Furthermore, the addition of the alkali metal hydroxide solution introduces water into an otherwise organic system. This causes the reaction to be conducted in a non-homogeneous multi-phase condition; and typically, it also requires the reaction to be conducted under an azeotropic condition. After the reaction, the removal of the high-boiling point water or alcohol also involves a tedious process; it requires a set of relatively complicated post-reaction equipment and is time-consuming. Thus, it is desirable to develop alternative processes for making epoxy resins for use in the microelectronic industry which involve simplified procedure and require reduced reaction time.

SUMMARY OF THE INVENTION

The primary object of the present invention is to develop polyphenol-derived epoxy resins which can be advantageously used in the microelectronic industry, and can be produced with a simplified procedure that requires reduced reaction time. Alternatively, the primary object of the present invention is to develop a simplified process for producing alternative epoxy resins, which would exhibit at least the same excellent properties as currently available materials, for use in the microelectronic industry. The phenolepoxy resins developed in the present invention can be most advantageously used in IC packaging, in making substrates for printed circuit boards, as adhesives for various electronic components, etc.

Unlike the conventional processes for making phenol-derived epoxy resins which require multiple reactants charging steps, the process disclosed in the present invention allows the raw materials of phenols and epihalohydrin to be added in the same step, along with the addition of an imidazole catalyst. Furthermore, the process disclosed in the present invention does not require any solvent, and it involves substantially simplified manufacturing equipment, and incurs substantially reduced reaction time. Thus the cost of producing phenol-derived epoxy resins can be substantially reduced.

The advantages of the present invention involve not only the cost-effectiveness of the process for making epoxy resins, but also the superior properties of the phenolepoxy resins that are made therefrom.

The phenolepoxy resins disclosed in the present invention can be represented by the following formula (I):

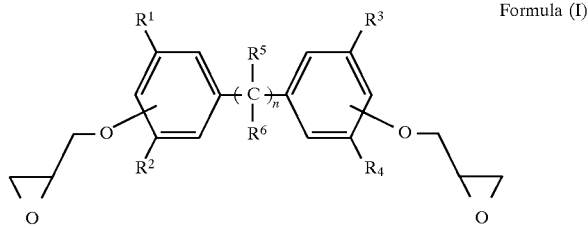

Formula (I)

where $R^1$, $R^2$, $R^3$, and $R^4$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; $R^5$ and $R^6$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups;

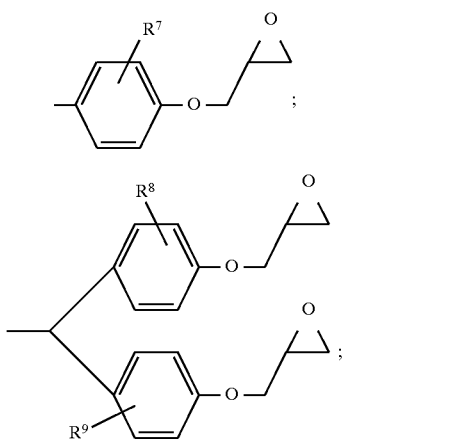

$R^7$ is hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; $R^8$ and $R^9$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; and n is an integer of 0 or 1.

DETAILED DESCRIPTION OF THE PREFERRED EMBODIMENT

The present invention discloses a family of new polyphenol-derived epoxy resins for use in the microelectronic industry which are produced with a simplified procedure requiring reduced reaction time relatively to the conventional processes. The phenolepoxy resins developed in the present invention can be most advantageously used, among other things, in IC packaging, in making substrates for printed circuit boards, as adhesives for various electronic components, etc. One of the advantages of the process disclosed in the present invention is that, unlike the conventional processes for making phenol-derived epoxy resins, the process of the present invention allows the raw materials of phenols and epihalohydrin to be added in the same step, along with the addition of an imidazole catalyst. Furthermore, the process disclosed in the present invention does not require any solvent, and it involves substantially simplified manufacturing equipment, and incurs substantially reduced reaction time. Thus the cost of producing phenol-derived epoxy resins can be substantially reduced.

The phenolepoxy resins disclosed in the present invention can be represented by the following formula (I):

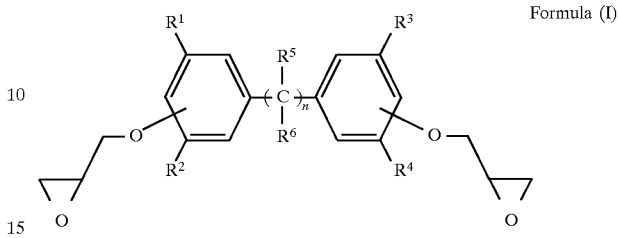

Formula (I)

where $R^1$, $R^2$, $R^3$, and $R^4$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; $R^5$ and $R^6$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups;

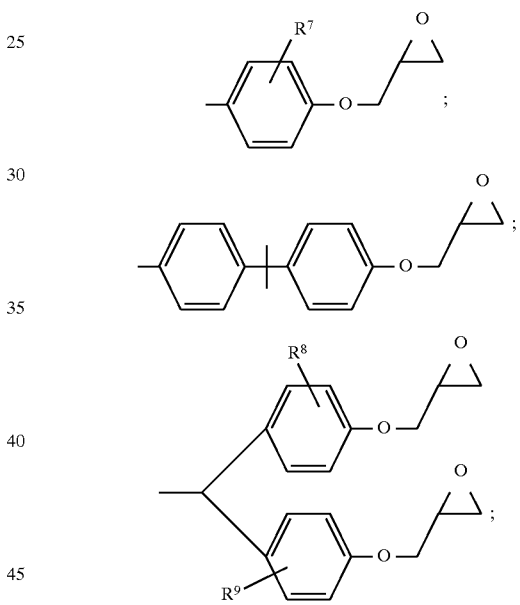

$R^7$ is hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; $R^8$ and $R^9$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_1O$ aromatic groups; and n is an integer of 0 or 1.

Preferably, $R^1$, $R^2$, $R^3$, and $R^4$, which can be the same of different, are hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, or $C_1$ to $C_6$ alkyl-, $C_1$ to $C_6$ cycloalkyl-, $C_2$ to $C_6$ alkenyl-, q to q alkynyl-substituted phenyl or naphthyl groups; more preferably, $R^1$, $R^2$, $R^3$, and $R^4$ are hydrogen, methyl, ethyl, n-propyl, iso-propyl, n-butyl, iso-butyl, tert-butyl, pentyl, hexyl, phenyl, toluyl, or ethylphenyl groups, or even more preferably, hydrogen, methyl, tert-butyl, or phenyl groups.

Preferably, $R^5$ and $R^6$, which can be the same or different, are hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, or $C_1$ to $C_6$ alkane-, $C_1$ to $C_6$ cycloalkyl-, $C_2$ to $C_6$ alkenyl-, $C_2$ to $C_6$ alkynyl-substituted benzene or naphthalene groups, more preferably, $R^5$ and $R^6$ are hydrogen, methyl, ethyl, n-propyl, iso-propyl, n-butyl, iso-butyl, tert-butyl, n-pentyl, iso-pentyl, neo-hexyl, hexyl, phenyl, toluyl, or ethylphenyl groups, or even more preferably, hydrogen, methyl, ethyl, n-propyl, or iso-propyl groups.

In Formula (I) shown above, the embodiments of $R^5$ and $R^6$ also include a radical represented by the following formula:

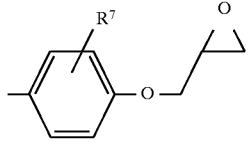

Preferably, $R^7$ is hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, or $C_1$ to $C_6$ alkyl-, $C_{1\ to\ C6}$ cycloalkyl-, $C_2$ to $C_6$ alkenyl-, $C_2$ to $C_6$ alkynyl-substituted phenyl groups, more preferably, $R^7$ is a methyl, ethyl, n-propyl, iso-propyl, n-butyl, iso-butyl, tert-butyl, pentyl, hexyl, or phenyl group.

The embodiments of $R^5$ and $R^6$ in Formula (I) also farther include a group represented by the following formula:

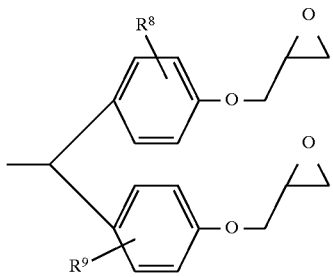

Preferably, $R^8$ and $R^9$, which can be the same or different, are hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, or $C_1$ to $C_6$ alkyl-, $C_1$ to $C_6$ cycloalkyl-, $C_2$ to $C_6$ alkenyl-, $C_2$ to $C_6$ alkynyl-substituted phenyl groups, more preferably, $R^8$ and $R^9$ are methyl, ethyl, n-propyl, iso-propyl, n-butyl, iso-butyl, tert-butyl, pentyl, hexyl, phenyl, or toluyl groups.

Combining the above discussions, the preferred embodiments of of $R^5$ and $R^6$ in Formula (I) include hydrogen, methyl, ethyl, n-pentyl, iso-pentyl, and the following radicals:

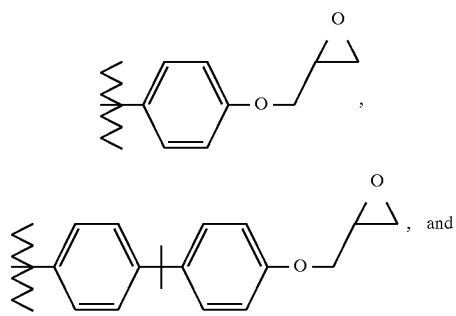

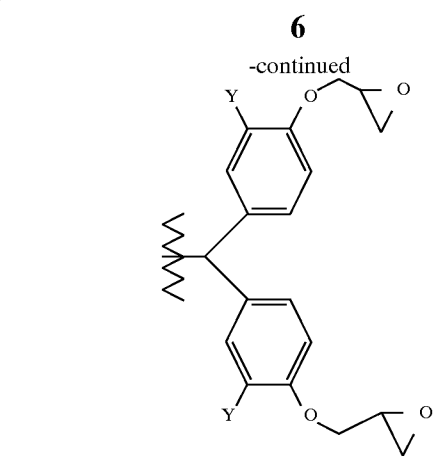

where Y is hydrogen or phenyl group.

The phenolepoxy resins disclosed above are prepared by reacting polyphenols with epihalohydrin in the presence of an imidazole catalyst. The polyphenols can be bi-, tri- or tetrapehnols, and alkyl or aromatic derivatives thereof. Preferably, the polyphenols are p, p' and o, o' polyphenols. During the reaction, the polyphenols are mixed with epihalohydrin and imidazole. Then the reaction mixture, which is in a homogeneous phase, is maintained at a reaction temperature between about 90° and about 120° C. The reaction time varies according to the substituted groups; typically, the reaction time is about 1 to 4 hours. The epihalohydrin can be either epichlorohydrin or epibromohydrin; however, epichlorohydrin is preferred. The amount of epihalohydrin should preferably between 1 and 20 equivalents per every equivalent of phenol group, or more preferably between 1 and 5 equivalents of epihalohydrin per every equivalent of phenol group. In the present invention, the imidazole catalyst is broadly defined to include imidazole and its derivatives. A variety of the imidazole-type compounds can be used as catalysts in the present invention. Preferred examples of imidazole-type catalysts include imidazole (1,3-diazole), 2-methylimidazole, 2-ethylimidazole, 2-n-propylimidazole, 2-isopropylimidazole, and 2-phenylimidazole. The amount of the imidazole catalyst should preferably between 0.01 and 0.5 equivalents per equivalent of phenol group, or more preferably between 0.01 and 0.2 equivalents per every equivalent of phenol group.

After the reaction, the reaction products can be added with 3 to 5 times by volume of an organic solvent, such as methyl ethyl ketone, 4-methyl-2-pentyl ketone, toluene, or mixtures thereof, and a 1N hydroxide solution of approximately the same volume. After stirring and refluxing for 1 to 4 hours, followed by extraction, drying, condensation, a raw product is obtained. The raw product so obtained can be re-crystalized using an organic solvent such as methyl ethyl ketone, 4-methyl-2-pentyl ketone, toluene, or ethanol, etc. The final product can be further purified using column chromatography and other techniques. The reaction yield can be as high as 85 to 95%.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

Preparation of 4,4'-bis(glycidyloxy-3,3'5,5'-tetramethylbiphenyl 48.4 g (0.20 mol) of 4,4'-dihydroxyl-3,3'5,5'-tetramethylbiphenyl, 0.68 g (0.01 mol) of imidazole, and 185.2 g (2.0 mol) of epichlorohydrin were added into a 500-ml reactor equipped with a mechanical stirrer and a cooling tube. The reactor was heated to 115° C. and the reactants were allowed to react under a reflux for two hours until the 3,3'5,5'-tetramethyl-4,4'-dihydroxylbiphenyl was completely reacted (as indicated by column chromatography). The reaction products were cooled to room temperature, and the excess epichlorohydrin was removed by a spinning condensation device.

200 ml of 4-methyl-2-pentyl ketone and 50 ml of 1N sodium hydroxide solution were added to the reaction product obtained above. The mixture was heated to 90° C., stirred and reacted under a reflux for 2 hours. After being cooled down to room temperature, the organic layer and the aqueous layer were separated via an extraction procedure. The organic content in the aqueous layer was further extracted using 4-methyl-2-pentyl ketone (160 ml, twice). The organic layers were then combined, dried with sodium sulfate anhydrite, filtration, and spin-condensed, obtain a raw product.

The raw product was re-crystalized using 4-methyl-2-pentyl ketone. 60.4 g of a white final solid product was obtained, indicating a reaction yield of 85%. The final product, which was 4,4'-bis(glycidyloxy)-3,3'5,5'-tetramethylbiphenyl, is represented by the following formula:

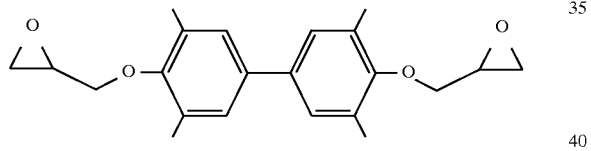

The melting point was measured to be 99.5°–101.5° C., and the NMR results obtained on this product are summarized as follows:

$^1$H NMR (CDCl$_3$, 200 MHz) δ 0.32 (12H, s), 2.72 (2H, dd, J=4.9, 2.7 Hz), 2.88 (2H, dd, J=4.9,4.4 Hz), 3.37 (2H, dddd, J=5.8, 4.4, 3.3, 2.7 Hz), 3.42 (2H, dd, J=11.0, 5.9 Hz), 4.06 (2H, dd, J=11.0, 3.3 Hz), 7.15 (4H, s).

$^{13}$C NMR (CDCl$_3$, 100 MHz) δ 15.8 (q), 51.3 (t), 51.7 (d), 73.2 (t), 128.2 (s), 130.9 (2C,d), 136.6 (2C, d), 154.8 (s).

EXAMPLE 2

Preparation of 4,4'-bis(glycidyloxy)biphenyl

The procedure in Example 2 was identical to that in Example 1, except that 4,4'-dihydroxyldiphenyl was used instead of 3,3'5,5'-tetramethyl-4,4'-dihydroxylbiphenyl, and that, during the purification step, the reaction product was extracted using a mixture of methyl ethyl ketone and toluene, instead of the 4-methyl-2-pentyl ketone used in Example 1. The raw product was further purified using methyl ethyl ketone to obtain a white solid product. The reaction yield was calculated to be 95%.

The final product, which was 4,4'-bis(glycidyloxy)biphenyl, is represented by the following formula:

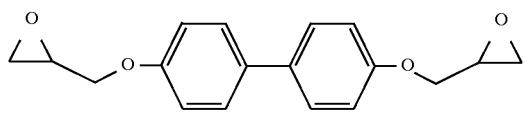

The melting point was measured to be 144°–146° C., and the NMR results obtained on this product are summarized as follows:

$^1$H NMR (CDCl$_3$, 200 MHz) δ 2.75 (2H, dd, J=4.9,2.6 Hz), 2.90 (2H, dd, J=4.9, 4.3 Hz), 3.36(2H, dddd,J=5.6,4.3, 3.0,2.6 Hz), 3.97 (2H, dd,J=11.1, 5.6Hz), 4.24(2H, dd,J= 11.1,3.0 Hz), 6.96 (4H, dd, J=8.7, 2.0 Hz), 7.44 (4H, dd, J=8.7, 2.0 Hz).

EXAMPLE 3

Preparation of 2,2'-bis(glycidyloxy)biphenyl

The procedure in Example 3 was identical to that in Example 1, except that, in addition to using a different polyphenol reactant (the polyphenol reactant should correspond to the final product, since this is well known in the art, this will not be elaborated), during the purification step, the reaction product was extracted using toluene, instead of the 4-methyl-2-pentyl ketone used in Example 1. The raw product was further purified by silica gel to obtain a colorless liquid product. The reaction yield was calculated to be 92%.

The final product, which was 2,2'-bis(glycidyloxy)biphenyl, is represented by the following formula:

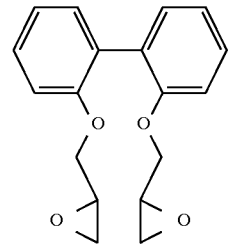

The NMR results obtained on this product are summarized as follows:

$^1$H NMR (CDCl$_3$, 200 MHz) δ 2.54 (2H, dd, J=5.1, 2.5 Hz), 2.70 (2H, dd, J=5.1, 4.0 Hz), 3.16 (2H, dddd,J=5.5,4.0, 2.9,2.5 Hz), 3.93 (2H, dd,J=11.2, 5.5 Hz), 4.17 (2H, dd,J= 11.2,2.9 Hz), 6.95 (2H, dd, J=8.1, <1.0 Hz), 7.03 (2H, dd, J=7.3, 1.0 Hz), 7.24 (4H, m).

$^{13}$C NMR (CDCl$_3$, 100 MHz) δ 44.3 (t), 50.2 (d), 68.9 (t), 112.6 (d), 121.0 (d), 128.3 (s), 128.5 (d), 131.4 (d), 155.9 (s).

EXAMPLES 4–7

The procedure in Examples 4–7 was identical to that in Example 1, except that, during the purification step, the reaction product was extracted using a mixture of methyl ethyl ketone and toluene, instead of the 4-methyl-2-pentyl ketone used in Example 1. The raw product was further re-crystalized using toluene to obtain white solid products. The reaction yields ranged from 85 to 90%.

EXAMPLE 4

Preparation of 2,2'-bis[(4-glycidyloxy-3,5-dimethyl)phenyl] propane

In Example 4, the reaction product, 2,2'-bis(4-glycidyloxy-3,5-dimethyl)phenyl propane, is represented by the following formula:

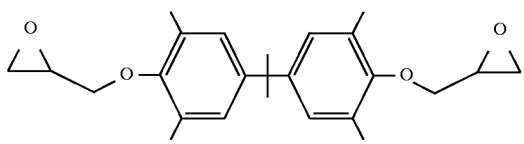

The NMR results obtained on this product are summarized as follows:
¹H NMR (CDCl₃, 200 MHz) δ 1.56 (6H, s), 2.15 (12H, s), 2.69 (2H, dd, J=4.9, 2.6 Hz), 2.85 (2H, dd, J=4.9,4.2 Hz), 3.33 (2H, dddd, J=5.9,4.2, 3.3, 2.6 Hz), 3.71 (2H, dd, J=11.0,5.9 Hz), 4.00 (2H, dd, J=11.0, 3.3 Hz), 6.80 (4H, s).

EXAMPLE 5

Preparation of 1,1'-bis[(4-glycidyloxy-3-phenyl)phenyl]propane

In Example 5, the reaction product, 1,1'-bis[(4-glycidyloxy-3-phenyl)phenyl]propane, is represented by the following formula:

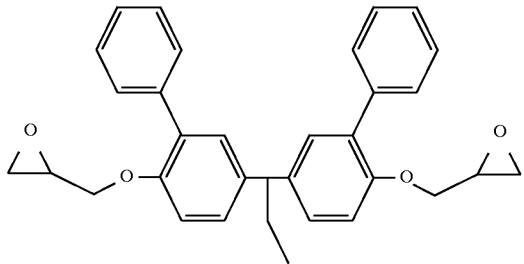

The NMR results obtained on this product are summarized as follows:
¹H NMR (CDCl₃, 400 MHz) δ 0.92 (3H, t, J=7.2 Hz), 2.06 (2H, dq, J=7.7, 7.2 Hz), 2.64 (2H, dd, J=4.9, 2.6 Hz), 2.78 (2H, dd, J=4.9, 4.4 Hz), 3.22 (2H, dddd, J=5.1, 4.4, 3.0, 2.6 Hz), 3.76 (1H, t, J=7.7 Hz), 3.93 (2H, dd, J=11.1, 5.1 Hz), 4.15 (2H, dd, J=11.1, 3.0 Hz), 6.89 (2H, d, J=8.4 Hz), 7.15 (2H, dd, J=8.4,2.2 Hz), 7.21 (2H, d, J=2.2 Hz), 7.30 (2H, tt,J=7.3, 2.0 Hz), 7.39 (4H, t, J=7.3 Hz), 7.52 (4H, dd, J=7.3, 2.0 Hz).

EXAMPLE 6

Preparation of 1,1'-bis[(4-glycidyloxy-3-phenyl)phenyl]butane

In Example 6, the reaction product, 1,1'-bis[(4-glycidyloxy-3-phenyl)phenyl]butane, is represented by the following formula:

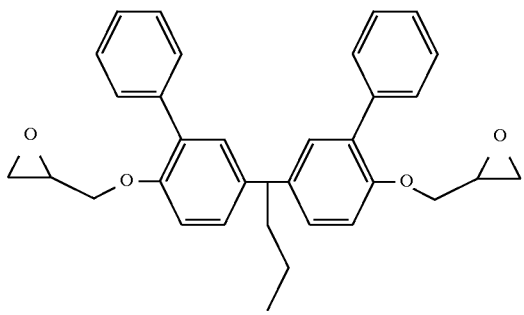

The NMR results obtained on this product are summarized as follows:
¹H NMR (CDCl₃, 200 MHz) δ 0.91 (3H, t, J=7.2 Hz), 1.27 (2H, tq, J=9.1, 7.2 Hz), 1.99 (2H, td, J=9.1, 4.8 Hz), 2.63 (2H, dd, J=4.9, 2.5 Hz), 2.76 (2H, dd, J=4.9, 4.4 Hz), 3.21 (2H, dddd, J=5.0, 4.4, 3.0, 2.5 Hz), 3.68 (1H, t, J=4.8 Hz), 3.93 (2H, dd, J=11.1, 5.0 Hz), 4.14 (2H, dd, J=11.1, 3.0 Hz), 6.87 (2H, d, J=8.3 Hz), 7.14 (2H, dd, J=8.3, 2.1 Hz), 7.20 (2H, d,J=2.1 Hz), 7.3 5 (6H, m), 7.51 (4H, dd, J=7.1, 1.7 Hz).

EXAMPLE 7

Preparation of 1,1'-bis[(4-glycidyloxy-3-phenyl)phenyl]-2-methylpropane

In Example 7, the reaction product, 1,1'-bis[(4-glycidyloxy-3-phenyl)phenyl]butane, is represented by the following formula:

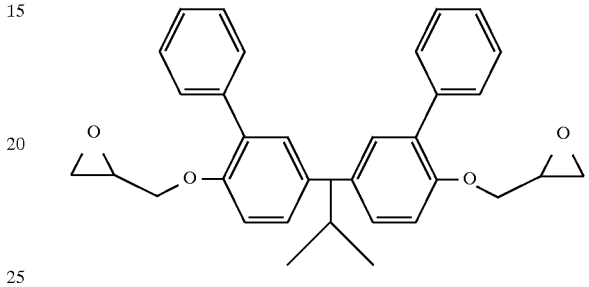

The NMR results obtained on this product are summarized as follows:
mp=131°–134° C.
¹HNMR(CDCl₃, 200 MHz) δ 0.83 (6H, d,J=6.5 Hz), 2.37 (1H, dsept,J=11.0,6.5Hz), 2.57 (2H, dd, J=4.9, 2.7 Hz), 2.71 (2H, dd, J=4.9, 4.4 Hz), 3.15 (2H, dddd, J=5.0,4.4,3.0,2.7 Hz), 3.31 (1H, t, J=11.0 Hz), 3.86 (2H, dd, J=11.1, 5.0 Hz), 4.07 (2H, dd, J=11.1, 3.0 Hz), 6.81 (2H, d, J=8.2 Hz), 7.12 (2H, dd, J=8.2,2.0 Hz), 7.20 (2H, d, J=2.0 Hz), 7.30 (6H, m), 7.45 (4H, dd, J=6.9, 1.7 Hz).

EXAMPLE 8

Preparation of 2,2'-bis[(4-glycidyloxy-3,3'5,5'-tetra-tert-butylbiphenyl

The procedure in Example 8 was identical to that in Example 1, except that (in addition to the appropriate starting polyphenol), during the purification step, the reaction product was recrystalized using ethanol to obtain a white solid product. The reaction yield was 85%. In Example 8, the reaction product, 2,2'-bis[(4-glycidyloxy-3,3',5,5'-tetra-tert-butylbiphenyl, is represented by the following formula:

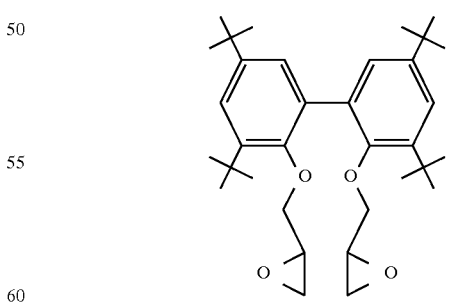

The NMR results obtained on this product are summarized as follows:
mp=185°–186° C.
¹H NMR (CDCl₃, 200 MHz) δ 1.33 (18H, s), 1.43 (18H, s), 2.19 (2H, dd, J=4.9, 2.7 Hz),2.63 (2H, dd, J=4.9, 4.4 Hz), 3.00 (2H, dddd, J=5.5,4.4, 3.3, 2.7 Hz), 3.57 (2H, dd, J=11.0

5.6 Hz), 3.68 (2H, dd, J=11.0, 3.3 Hz), 7.14 (2H, d, J=2.4Hz), 7.38 (2H, d, J=2.4 Hz).

MS (m/e): 522 (M$^+$, base), 466 (base), 451, 337, 225, 57, 41, 29.

EXAMPLES 9–11

The procedure in Examples 9–11 was identical to that in Example 1, except that (in addition to the polyphenol reactants), the amounts of epichlorohydrin and imidazole were increased to 1.5 times as much and, during the extraction step, the amount of sodium hydroxide solution was also increased to 1.5 times. The reaction product was extracted with 4-methyl-2-pentyl ketone, and then concentrated to obtain white semi-solid products. The reaction yields ranged from 85 to 90%.

EXAMPLE 9

Preparation of tris(4-glycidyloxyphenyl)methane

In Example 9, the reaction product, tris(4-glycidyloxyphenyl)methane, is represented by the following formula:

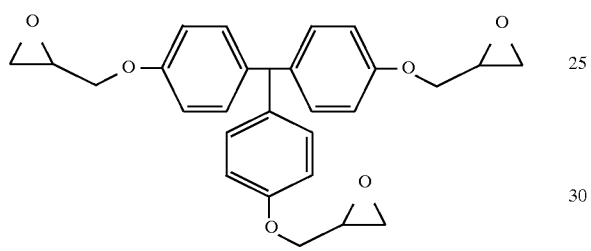

The NMR results obtained on this product are summarized as follows:

$^1$H NMR (CDCl$_3$, 200 MHz) δ 2.72 (3H, dd, J=4.9,2.7 Hz), 2.87 (3H, dd, J=4.9,4.2 Hz), 3.31 (3H, dddd, J=5.5, 4.2, 3.1, 2.7 Hz), 3.92 (3H, dd, J=11.0, 5.5 Hz), 4.16 (3H, dd, J=11.0, 3.1 Hz), 5.37 (1H, s), 6.81 (6H, dd, J=8.6, 2.5 Hz), 6.97 (6H, dd, J=8.6, 2.5 Hz).

EXAMPLE 10

Preparation of bis[(4-glycidyloxy-3-phenyl)phenyl]-(4-glycidyloxyphenyl)methane

In Example 10, the reaction product, bis[(4glycidyloxy-3-phenyl)phenyl]-(4-glycidyloxyphenyl)methane, is represented by the following formula:

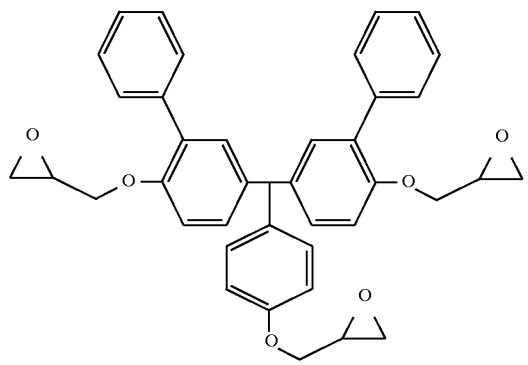

The NMR results obtained on this product are summarized as follows:

$^1$H NMR (CDCl$_3$, 200 MHz) δ 2.58 (2H, dd, J=4.9,2.7 Hz), 2.66 (1H, dd, J=4.9,2.6 Hz), 2.71 (2H, dd, J=4.9, 4.0 Hz), 2.81 (1H, dd, J=4.9, 4.2 Hz), 3.16 (2H, dddd, J=5.0, 4.0, 3.0, 2.7 Hz), 3.25 (1H, dddd, J=5.5, 4.2, 3.0, 2.6 Hz), 3.86 (1H, dd, J=11.1, 5.5 Hz), 3.87 (2H, dd, J=11.1, 5.0 Hz), 4.10 (3H, dd, J=11.1, 3.0 Hz), 5.39 (1H, s), 6.76 (2H, d, J=8.9 Hz), 6.81 (2H, d, J=8.4 Hz), 6.94 (2H, dd, J=8.4,2.2 Hz), 6.99 (2H, d, J=8.9 Hz), 7.05 (2H, d, J=2.2 Hz), 7.25 (6H, m), 7.41 (4H, dd, J=6.9, 2.0 Hz).

MS (m/e): 612 (M$^+$, base), 539, 536, 463, 387, 298, 273, 197, 31.

EXAMPLE 11

Preparation of 1-[α-methyl-α-(4-glycidyloxyphenyl)ethyl]-4-[α, α-bis(4-glycidyloxyphenyl)ethyl]benzene In Example 11, the reaction product, 1-[α-methyl-α-(4-glycidyloxyphenyl)ethyl]-4-[α, α-bis(4-glycidyloxyphenyl)ethyl]benzene, is represented by the following formula:

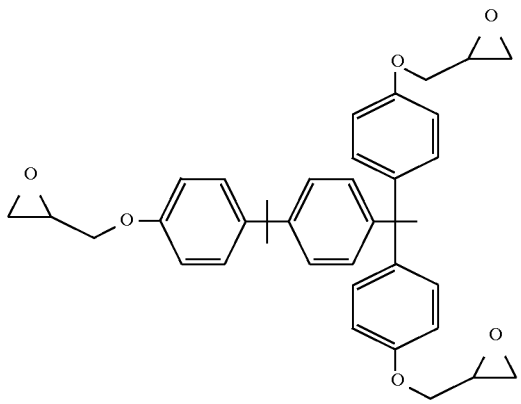

The NMR results obtained on this product are summarized as follows:

$^1$H NMR (CDCl$_3$, 200 MHz) δ 1.57 (6H, s), 2.02 (3H, s), 2.67 (3H, dd, J=4.9, 2.5 Hz), 2.82 (3H, dd, J=4.9,4.4 Hz), 3.26 (3H, dddd, J=5.4,4.4,3.3,2.5 Hz), 3.87 (3H, dd, J=11.0, 5.4 Hz), 4.11 (3H, dd, J=11.0, 3.3 Hz), 6.72 (4H, d, J=8.8 Hz), 6.75 (2H, d, J=8.6 Hz), 6.86 (2H, d, J=8.8 Hz), 6.91 (4H, d, J=8.8 Hz), 7.01 (2H, d, J=8.6 Hz), 7.08 (2H, d, J=8.8 Hz).

EXAMPLES 12–13

The procedure in Examples 12–13 was identical to that in Example 1, except that, the amounts of epichlorohydrin and imidazole were increased to twice as much and, during the extraction step, the amount of sodium hydroxide solution was also doubled. After extraction and condensation, the reaction product was re-crystalized using 4-methyl-2-pentyl ketone to obtain white solid products. The reaction yields ranged from 85 to 87%.

EXAMPLE 12

Preparation of 1,1'-2,2'-tetrakis(4-glycidyloxyphenyl)ethane

In Example 12, the reaction product, 1,1'-2,2'-tetrakis(4-glycidyloxyphenyl)ethane, is represented by the following formula:

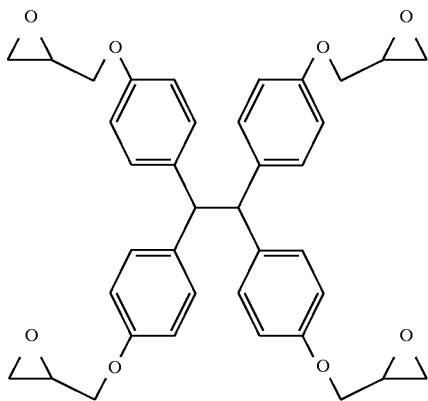

The NMR results obtained on this product are summarized as follows:

$^1$H NMR (CDCl$_3$, 200 MHz) δ 2.67 (4H, dd, J=4.9,2.6 Hz), 2.83 (4H, dd, J=4.9,4.4 Hz), 3.25 (4H, dddd, J=5.6, 4.4, 3.3, 2.6 Hz), 3.81 (4H, dd, J=11.0, 5.6 Hz), 4.06 (4H, dd, J=11.0, 3.3 Hz), 4.52 (2H, s), 6.64 (8H, d, J=8.5 Hz), 6.95 (8H, d, J=8.5 Hz).

MS (m/e): 622 (M$^+$), 473, 347, 311 (base), 255, 136, 107, 57.

EXAMPLE 13

Preparation of 1,1'-2,2'-tetrakis[(4-glycidyloxy-3-phenyl)phenyl]ethane

In Example 12, the reaction product, 1,1'-2,2'-tetrakis[(4-glycidyloxy-3-phenyl)phenyl)]ethane, is represented by the following formula:

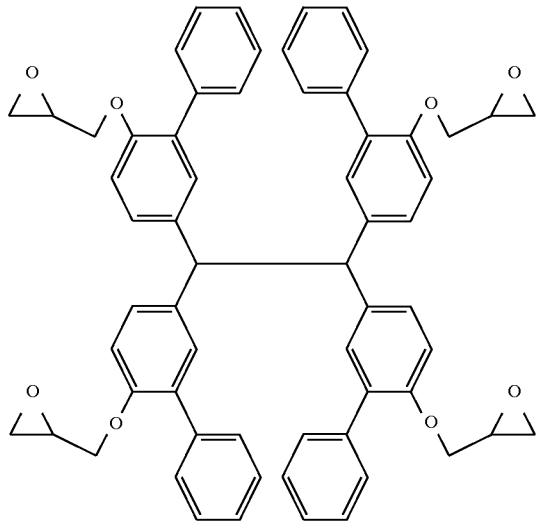

The NMR results obtained on this product are summarized as follows:

$^1$H NMR (CDCl$_3$, 200 MHz) δ 2.67 (4H, dd, J=4.9, 2.5 Hz), 2.82 (4H, dd, J=4.9,4.4 Hz), 3.24(4H,dddd,J=5.5,4.4, 3.3,2.5Hz),3.85 (4H,dd,J=11.1,5.5 Hz), 4.08 (4H,dd, J=11.1, 3.3 Hz), 4.53 (2H, s), 6.80 (4H, d, J=8.2 Hz), 7.10 (4H, dd, J=8.2, 2.1 Hz), 7.20 (4H, d, J=2.1 Hz), 7.31 (12H, m), 7.44 (8H, dd, J=7.0, 1.8 Hz).

For completeness of the this disclosure, the starting polyphenols for the above examples are: 4,4'-bis(hydroxy)-3,3'5,5'-tetramethylbiphenyl; 4,4'-bis(hydroxy)biphenyl; 2,2'-bis(hydroxy)biphenyl; 2,2'-bis[(4-hydroxy-3,5-dimethyl)phenyl]propane; 1,1'-bis[(4-hydroxy-3-phenyl)phenyl]propane; 1,1 '-bis[(4-hydroxy-3-phenyl)phenyl]butane; 1,1 '-bis[(4-hydroxy-3-phenyl)phenyl]-2-methylpropane; 2,2'-bis[(4-hydroxy-3,3',5,5'-tetra-tert-butylbiphenyl; tris(4-hydroxyphenyl)methane; bis[(4-hydroxy-3-phenyl)phenyl]-(4-hydroxyphenyl)-methane; 1-[α-methyl-α-(4-hydroxyphenyl)ethyl]-4-[α, α-bis(4-hydroxyphenyl)ethyl]benzene; 1,1 '-2,2'-tetrakis(4-hydroxyphenyl)ethane; and 1,1 '-2,2'-tetrakis[(4-hydroxy-3-phenyl)phenyl)]ethane, respectively.

The phenolepoxy resins prepared above exhibited low viscosity, excellent heat-resistance, and low moisture absorption, and thus are excellent materials to be used in IC packaging, encapsulation, making printed circuit boards, and as adhesives in the electronics industry. Compared to the conventional methods, the phenolepoxy resins of the present invention can be made in a process that involves a single feed-charging step, can be conducted in room pressure under reflux, and does not require any solvent. The process disclosed in the present invention for preparing the phenolepoxy resins also provides many other advantages relative to the conventional process in that it requires simplified production facility, involves much simplified procedure, incurs reduced reaction time, and provides high production yields.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for preparing phenolepoxy resin represented by the following formula (I):

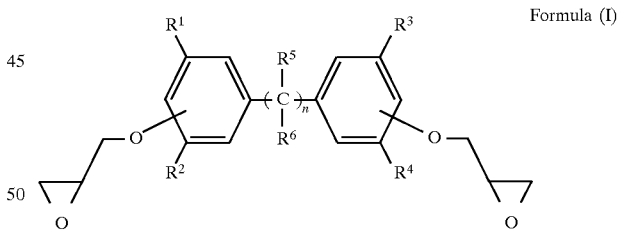

Formula (I)

wherein, (a) R$^1$, R$^2$, R$^3$, and R$^4$, which can be the same or different, are hydrogen, C$_1$ to C$_6$ alkyl groups, C$_6$ to C$_{10}$ aromatic groups, or C$_1$ to C$_6$ alkyl group-substituted C$_6$ to C$_{10}$ aromatic groups; (b) R$^5$ and R$^6$, which can be the same or different, are hydrogen, C$_1$ to C$_6$ alkyl groups, C$_6$ to C$_{10}$ aromatic groups, or C$_1$ to C$_6$ alkyl group-substituted C$_6$ to C$_{10}$ aromatic groups;

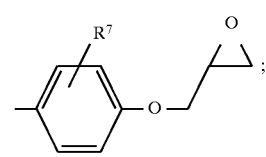

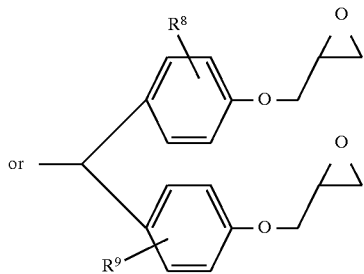

(c) $R^7$ is hydrogen, $C_1$ to $C_6$ alkyl groups, $C_1$ to $C_{10}$ aromatic groups, or $C_1$ to $C_6$ alkyl group-substituted $C_6$ to $C_{10}$ aromatic groups; (d) $R^8$ and $R^9$, which can be the same or different, are hydrogen, $C_1$ to $C_6$ alkyl groups, $C_6$ to $C_{10}$ aromatic groups, or $C_1$ to $C_6$ alkyl group-substituted $C_6$ to $C_{10}$ aromatic groups; and (e) n is an integer of 0 or 1; said method comprising the step of:

(i) preparing a reaction medium consisting essentially of at least one polyphenol, an epihalohydrin, and an imidazole catalyst;

(ii) causing said reaction medium to react in the absence of any aqueous phase;

(iii) wherein between about 1 and about 20 equivalents of said epihalohydrin and between about 0.01 and about 0.5 equivalents of said imidazole catalyst are added in said reaction medium per every equivalent of phenol group.

2. The method for preparing phenolepoxy resin according to claim 1, wherein said at least one polyphenol is selected from the group consisting of bi-, tri- and tetraphenols, and alkyl or aromatic derivatives thereof.

3. The method for preparing phenolepoxy resin according to claim 1, wherein said epihalohydrin is epichlorohydrin or epibromohydrin.

4. The method for preparing phenolepoxy resin according to claim 1, wherein between about 1 and 5 equivalents of epihalohydrin are added per every equivalent of phenol group.

5. The method for preparing phenolepoxy resin according to claim 1, wherein said imidazole catalyst is selected from the group consisting of 1,3-diazole, 2-methylimidazole, 2-ethylimidazole, 2-n-propylimidazole, 2-isopropylimidazole, and 2-phenylimidazole.

6. The method for preparing phenolepoxy resin according to claim 1, wherein between about 0.01 and about 0.2 equivalents of said imidazole catalyst is added per equivalent of phenol group.

* * * * *